United States Patent
Bredno et al.

(10) Patent No.: US 8,295,573 B2
(45) Date of Patent: Oct. 23, 2012

(54) MOTION-COMPENSATED CORONARY FLOW FROM PROJECTION IMAGING

(75) Inventors: Joerg Bredno, Aachen (DE); Juergen Weese, Aachen (DE); Alexandra Groth, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 932 days.

(21) Appl. No.: 12/301,639

(22) PCT Filed: May 14, 2007

(86) PCT No.: PCT/IB2007/051811
§ 371 (c)(1), (2), (4) Date: Nov. 20, 2008

(87) PCT Pub. No.: WO2007/135612
PCT Pub. Date: Nov. 29, 2007

(65) Prior Publication Data
US 2009/0116715 A1 May 7, 2009

(30) Foreign Application Priority Data
May 22, 2006 (EP) .................................... 06114294

(51) Int. Cl.
*G06K 9/00* (2006.01)
(52) U.S. Cl. ........ 382/130; 382/103; 382/107; 382/128; 382/131; 600/431
(58) Field of Classification Search .................. 382/130, 382/103, 107, 131, 128; 600/431
See application file for complete search history.

(56) References Cited

U.S. PATENT DOCUMENTS

| | | | |
|---|---|---|---|
| 2005/0083053 | A1 | 4/2005 | Foo |
| 2005/0085707 | A1 | 4/2005 | Maria Korsten et al. |
| 2005/0187462 | A1 | 8/2005 | Koh et al. |
| 2006/0058674 | A1 | 3/2006 | Olstad |

FOREIGN PATENT DOCUMENTS

| | | |
|---|---|---|
| WO | 9631156 A1 | 10/1996 |
| WO | 0202173 A1 | 1/2002 |
| WO | 03043516 A2 | 5/2003 |
| WO | 03046797 A2 | 6/2003 |
| WO | 2005039253 A1 | 4/2005 |

OTHER PUBLICATIONS

Stuke I et al: "Cardio dynamic subtraction angtography (CDSA)" Second Joint EMBS-BMES Conference 2002. Conference Proceedings. 24th. Annual International Conference of the Engineering in Medicine and Biology Society. Houston TX, vol. 1 of 3. Conf. Oct. 23, 2002, pp. 915-916, XP010619884 ISBN: 0-7803-7612-9.
Shpilfoygel Simon D et al: "X-ray videodensitometric methods for blood flow and velocity measurement: A critical review of literature" Medical Physics, AIP, Melville, NY, US, vol. 27, No. 9, Sep. 2000, pp. 2008-2023, XP012011255 ISSN: 0094-2405.

(Continued)

*Primary Examiner* — Long Pham

(57) ABSTRACT

Diagnostic angiograms only provide the projected lumen of a coronary, which is only an indirect measure of blood flow and pressure decline. According to an exemplary embodiment of the present invention, a motion compensated determination of a flow dynamics and a pressure decline for stenosis grading is provided, in which the motion compensation is performed on the basis of a tracking of a first position of a first marker and a second position of a second marker in the projection data set. This may provide for a robust and precise flow dynamics and pressure decline determination.

17 Claims, 2 Drawing Sheets

OTHER PUBLICATIONS

Kawal S. Rhode, et al: Novel Approaches to the Measurement of Arterial Blood Flow From Dynamic Digital X-ray Images, IEEE Transactions on Medical Imaging, vol. 24, No. 4, Apr. 2005, pp. 500-513.

M. Mischi, et al: Intra-Thoracic Blood Volume Assessment by Dilution of Ultrasound Contrast Agents, 2003 IEEE Ultrasonics Symposium, pp. 1179-1182.

Hoffman KR, et al: A System for determination of 3D vessel tree centerlines from biplane images, International Journal of Cardiac Imaging, vol. 16, No. 5, 2000, pp. 315-330.

Baert S, et al: Guide wire tracking during endovascular interventions, in Delp SL, DiGioia AM, Jaramaz B, (eds.): MICCAI 2000, Proc. LNCS 1935, pp. 727-734, 2000.

Aach T. et al: Statistical-Model based identification of complete vessel-tree frames in coronary angiograms, Bouman CA and Miller EL (eds.), Electronic imaging 2004: Computational imaging, Proc, SPIE 5299, pp. 283-294, 2004.

MOTION-COMPENSATED CORONARY FLOW FROM PROJECTION IMAGING

FIELD OF THE INVENTION

The invention relates to the field of medical imaging. In particular, the invention relates to an examination apparatus for motion compensated determination of flow dynamics from an image sequence of an object of interest, to a method of motion compensated determination of flow dynamics, an image processing device, a computer-readable medium and a program element.

TECHNICAL BACKGROUND

Stenosis grading from contrasted x-ray angiograms is of major interest for minimally invasive treatment of diseased coronaries in the cardiac cathlab. Obstructed volume flow and increased pressure decline at a coronary lesion are the major cause of coronary heart disease. For a well founded treatment decision, it is important in daily clinical routine to assess the severity of such stenoses. Currently, subjective visual inspection of coronary angiograms or the determination of the pressure decline using an intravascular pressure gauge are used to assess this severity. Coronaries move with heart beat and respiration of a patient such that a separation between the movement of the vessels themselves and the flow of blood inside the vessels is required for a clinically valid assessment.

SUMMARY OF THE INVENTION

It would be desirable to have a motion compensated determination of coronary flow.

It should be noted that the following described exemplary embodiments of the invention apply also for the method, the computer-readable medium, the image processing device and the program element.

According to an exemplary embodiment of the present invention, an examination apparatus for motion compensated determination of flow dynamics from an image sequence of an object of interest is provided, the examination apparatus comprising an analysis unit adapted for performing a determination of a first volume flow in a region of the object of interest, wherein the determination comprises a motion compensation performed on the basis of a tracking of a first position of a first marker in the image sequence, wherein a motion of the marker corresponds to a motion of the object of interest.

Therefore, the examination apparatus may be adapted to determine a motion and therefore, e.g., a volume flow, fluid characteristics or transient properties in a region, which may, for example, be a coronary artery. In order to determine the flow dynamics, the position of a first marker, which is present in the region of the object of interest, is detected in the image sequence. This marker is adapted for marking the region of interest (i.e. a vessel segment of interest).

It should be noted, however, that further markers may be present. For example, a second marker may be provided which position in the image sequence is tracked as well. Thus, not only a linear motion may be determined and compensated for, but also a rotation of the structure comprising the two markers. If, for example, a third marker is tracked as well, a three-dimensional movement of the structure (such as a bending or deformation) may be determined and compensated for.

It should be noted, that the terms "motion compensation" or "motion compensated determination" also refer to "deformation compensation" or "deformation compensated determination".

According to another exemplary embodiment of the present invention, the examination apparatus further comprises an acquisition unit adapted for acquiring the image sequence in one of a dedicated flow run and a standard acquisition run.

Therefore, according to this exemplary embodiment of the present invention, the motion compensated flow determination may be performed on either a data set which is acquired particularly for such determination process, or on the basis of a standard data set which is acquired during a normal examination process.

According to another exemplary embodiment of the present invention, the image sequence or data set is acquired according to the following scheme: acquisition of first image data without contrast agent, application of a small diluted amount of contrast agent, and subsequent acquisition of second image data corresponding to an in- and outflow of the contrast agent during a multitude of cardiac cycles.

Thus, the diluted contrast agent that does not obscure the markers is observed during in- and outflow through the object of interest directly after and together with the first "empty" heartbeat in one acquisition with no stop and restart of the imager in between.

According to another exemplary embodiment of the present invention, the image sequence is an angiogram data set.

Therefore, a flow determination for coronary stenosis grading may be provided on the basis of angiogram data.

According to another exemplary embodiment of the present invention, the motion compensation comprises the use of heartbeat data or respiration (or exhalation) data.

Thus, motion compensation may not only be performed on the basis of the first and second marker positions, but may also be performed on the basis of electrocardiogram data (if the heart of a patient is imaged) or on the basis of breathing data (in case, for example, the lung of a patient is imaged).

The method may also be applied to vessels in the lung. However, a main field of application of the invention is the compensation of respiration motion where the heart beats itself but is also deformed and shifted around by respiration. The application of the invention may thus include a compensation of heart beat motion, a compensation of respiration motion, a compensation of voluntary and non voluntary patient motion and any combination thereof.

According to another exemplary embodiment of the present invention, the analysis unit is further adapted for determining a time intensity curve of contrast agent concentration on the basis of at least the first position of the first marker and a second position of a second marker, and performing a model-based flow analysis adapted to determine at least one of a total volume flow and a pressure decline, even in the presence of strong pulsation effects.

Therefore, by collecting time intensity curves of contrast agent concentration from at least two well-defined points in a moving coronary, a model-based flow analysis adapted for total volume flow determination, pressure decline and further relevant parameters in a vessel may be possible, even in the presence of strong pulsation effects.

According to another exemplary embodiment of the present invention, the model-based flow analysis includes varying flow speeds over the cardiac cycle and compensates for such pulsatility when electrocardiogram data is available as input.

According to another exemplary embodiment of the present invention, the object of interest is a coronary artery, wherein the region of the object of interest is a first vessel segment of the coronary artery.

Furthermore, the first and second markers may be adapted as distance markers of one of a guide wire, a semi-transparent guide wire, a stenting device and a ballooning device.

Therefore, according to this exemplary embodiment of the present invention, an interventional device with at least two detectable markers is present in the coronary and may allow for a marking of the vessel segment of interest.

According to another exemplary embodiment of the present invention, the analysis unit is further adapted for compensating a variability of the first volume flow over the cardiac cycle by one of a defined time of contrast agent injection or by an inclusion and compensation of the variability in a subsequent analysis.

According to another exemplary embodiment of the present invention, the subsequent analysis is a videodensitometric analysis.

According to still another exemplary embodiment of the present invention, the determination is further adapted for determining a second volume flow in a second vessel segment of the coronary artery and for determining a pressure decline in the first vessel segment on the basis of the second volume flow.

Therefore, according to this embodiment, not only a flow dynamics or a volume flow in the first vessel segment may be determined, but also a pressure change. This may provide for an improved stenosis grading.

According to another exemplary embodiment of the present invention, the examination apparatus is adapted as one of three-dimensional computed tomography apparatus and a three-dimensional rotational x-ray apparatus.

According to another exemplary embodiment of the present invention, the examination apparatus is configured as one of the group consisting of a material testing apparatus (such as, for example, an apparatus adapted for an assessment of fluid dynamics in moving components such as combustion engines) and a medical application apparatus in order to image a sequence showing flow phenomena in moving tubes or containers. A field of application of the invention may be medical imaging.

According to another exemplary embodiment of the present invention, a method of motion compensated determination of flow dynamics from an image sequence of an object of interest with an examination apparatus may be provided, the method comprising the step of determining a flow dynamics in a region of the object of interest, wherein the determination comprises a motion compensation performed on the basis of a tracking of a first position of a first marker in the image sequence, wherein a motion of the marker corresponds a motion of the object of interest.

This may provide for a robust and precise flow dynamics analysis.

According to another exemplary embodiment of the present invention, an image processing device for motion compensated determination of a flow dynamics may be provided, the image processing device comprising a memory for storing an image sequence of the object of interest and an analysis unit adapted for carrying out the above-mentioned method steps.

According to another exemplary embodiment of the present invention, a computer-readable medium may be provided, in which a computer program of motion compensated determination of a flow dynamics from an image sequence of an object of interest is stored which, when being executed by a processor, causes the processor to carry out the above-mentioned method steps.

Furthermore, according to another exemplary embodiment of the present invention, a program element of motion compensated determination of a flow dynamics may be provided, which, when being executed by a processor, causes the processor to carry out the above-mentioned method steps.

It should be noted that the method of examination of the object of interest (comprising the motion compensated determination of the flow dynamics) may be embodied as the computer program, i.e. by software, or may be embodied using one or more special electronic optimisation circuits, i.e. in hardware, or the method may be embodied in hybrid form, i.e. by means of software components and hardware components.

The program element according to an exemplary embodiment of the invention is preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the World Wide Web, from which it may be downloaded into image processing units or processors, or any suitable computers.

It may be seen as the gist of an exemplary embodiment of the present invention that a determination of a flow and of a pressure decline in a coronary artery from dynamic coronary angiograms is performed, wherein the angiograms are either acquired in a dedicated flow run or as standard diagnostic acquisition. Determination of the flow and the pressure decline is performed by using an interventional device with at least two detectable markers adapted for marking the vessel segment of interest. In this exemplary embodiment, preferably the markers are taken from a device which is already present in a coronary of interest during a minimally invasive treatment under x-ray control. This may provide for a robust and precise flow and pressure decline determination.

These and other aspects of the present invention will become apparent from and elucidated with reference to the embodiments described hereinafter.

BRIEF DESCRIPTION OF THE DRAWINGS

Exemplary embodiments of the present invention will be described in the following, with reference to the following drawings.

DETAILED DESCRIPTION OF EXEMPLARY EMBODIMENTS

Figure 1:
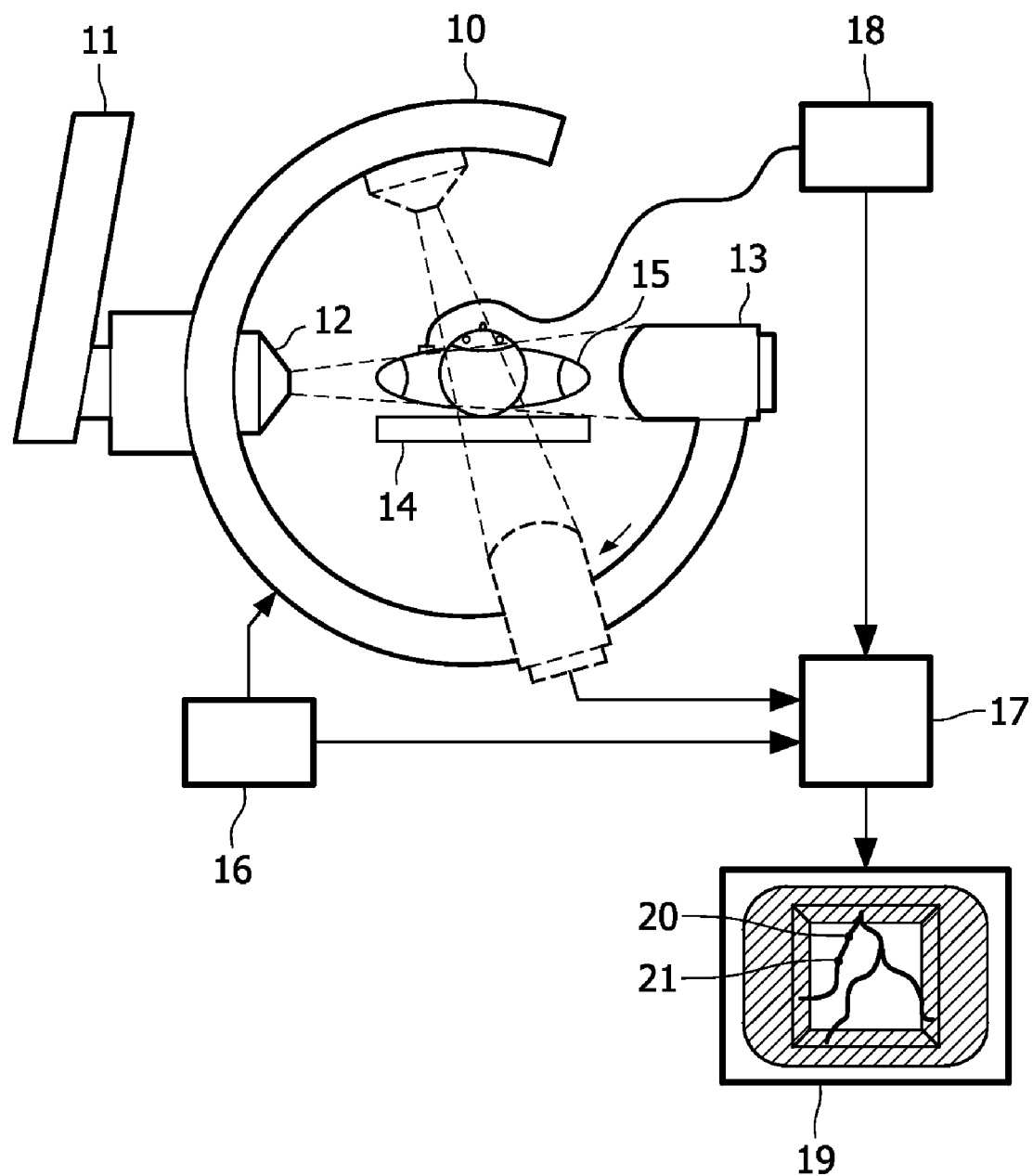
FIG. 1 shows a simplified schematic representation of an examination apparatus according to an exemplary embodiment of the present invention.

The illustration in the drawings is schematic. In different drawings, similar or identical elements are provided with the same reference numerals.

FIG. 1 shows a simplified schematic representation of an examination apparatus according to an exemplary embodiment of the present invention.

The invention may be applied in the field of two-dimensional imaging like fluoroscopic x-ray, x-ray angiograms, ultrasound, or video-imaging. In such a case, the examination may be performed with conventional x-ray systems. Furthermore, the invention may be applied in the field of three-dimensional imaging, such as three-dimensional rotational x-ray imaging or three-dimensional rotational angiography imaging.

The invention may be particularly used when a motion compensated coronary flow has to be determined from projection imaging but may as well be used when a change of pressure has to be detected in a vessel.

The apparatus depicted in FIG. 1 is a C-arm x-ray examination apparatus, comprising a C-arm 10 attached to a ceiling (not depicted in FIG. 1) by means of an attachment 11. The C-arm 10 holds the x-ray source 12 and the detector unit 13. The control unit 16 is adapted for controlling the acquisition process.

The image data generated by the detector unit 13 is transmitted to image processing unit 17 which is controlled by a computer.

Furthermore, an electrocardiogram (ECG) unit 18 may be provided for recording the heartbeat of the patient's heart. The corresponding ECG data is then transmitted to the image processing unit 17. Furthermore, exhalation data may be recorded and transmitted to the image processing unit 17.

The image processing unit 17 is adapted to carry out the above-mentioned method steps.

Furthermore, the system may comprise a monitor 19 adapted for visualising the acquired images. Monitor 19 shows a vessel comprising two markers 20, 21 in one vessel arm.

The invention relates mainly to sequences of 2D image data but may also be applied to sequences of 3D image data as created by computed tomography, or magnetic resonance imagers.

Figure 2:
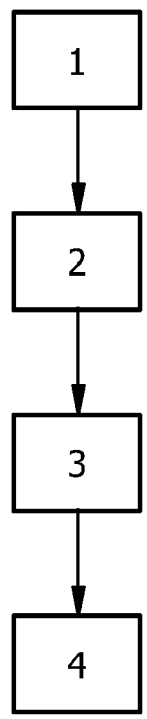
FIG. 2 shows a flow-chart of an exemplary method according to the present invention.

FIG. 2 shows a flow-chart of an exemplary method according to the present invention.

Interventional assessment of coronary blood flow is of major interest for coronary stenosis grading and outcome control, i.e. for interventions due to coronary heart disease. However, diagnostic angiograms only provide the projected lumen of a coronary, which is only an indirect measure of blood flow and pressure decline.

It is desired to assess the flow resistance and residual flow volume of a coronary stenosis objectively from angiogram sequences without relying on an observer's visual impression of the projected vessel lumen or the use of additional interventional devices. Image analysis to determine blood flow from projections based on videodensitometric methods is described in Shpilfoygel SD, Close RA, Valentino D J, Duckwiler G R, "X-ray videodensitometric methods for blood flow and velocity measurement: A critical review of literature", Medical Physics 27(9), pp 2008-2023, 2000, but has so far not been successfully transferred to a useful clinical system applicable to coronaries.

The application of videodensitometric methods that allow to objectively assess blood flow through coronaries from projection angiograms may require to compensate for the following sources of deviation: Cardiac contraction leading to a complex deformation of coronaries, respiration motion leading to a motion of the heart in the rib cage, foreshortening artifacts of the non-planar vessel geometry, and variabilities of the flow volume due to radius and driving pressure changes over the cardiac cycle.

Furthermore, the robustness and precision of algorithms for videodensitometric flow analysis may be limited. The method according to the invention addresses all above difficulties and may therefore enable videodensitometric blood flow assessment for coronaries during Cathlab interventions.

According to a first embodiment, a dedicated flow acquisition protocol is acquired.

In step 1, a guidewire with distance markers is located over a vessel segment of interest. In step 2, a diagnostic angiogram with diluted contrast agent is acquired during breath-hold of the patient. Then, in step 3, the markers on the guidewire are extracted and define fixed positions in the moving coronary with a well-defined distance in the vessel segment of interest. Time-intensity-curves for the concentration of contrast agent at these positions are then extracted for videodensitometric analyses (step 4). A model-based flow analysis may include varying flow speeds over the cardiac cycle and compensate for such pulsatility when ECG is available as input.

Extensions of this basic method may include the application of available methods to compensate for cardiac and respiration motion for the markers to determine their position even when they are obscured by contrast agent.

Such cardiac motion compensation is described in WO2005039253 A1, Konink Philips Electronics NV, Philips Intellectual Property GMBH, "Angiographic image providing device for operating vascular system, generates angiogram image related to matching between heartbeat phase with given heartbeat phase based on function describing position of heart", Bredno J, Eck K, Rongen P.

This may allow to apply the same method to standard angiograms in which the vessels are fully opacified and even if the patient did not hold his breath during the acquisition.

For both embodiments, variabilities of the volume flow over the cardiac cycle are compensated either by a defined time of contrast agent injection or by inclusion and compensation of this effect in the subsequent videodensitometric analyses.

As a first step for flow and stenosis assessment, it may be necessary to identify at least two points that remain fixed in a coronary during heartbeat and respiration motion. These markers may be, for example, located up- and downstream of a suspicious vessel segment, respectively. The tracking of markers as e.g. provided by an interventional device (as described in Florent R, Nosjean L, Lelong P, "Medical viewing system and method for enhancing structures in noisy images", WO 03/043516 A2, 2003) or the guidewire segmentation (as described in Baert S, Niessen W J, Meijering E H W, Frangi A F, Viergever A F, "Guide wire tracking during endovascular interventions," in Delp S L, DiGioia A M, Jaramaz B(eds.): MICCAI 2000, Proc. LNCS 1935, pp. 727-734, 2000) may be able to provide such marker positions as long as no or only little contrast agent is present in the vessels. This, however, may contradict current clinical protocols that aim for strongly opacified vessels.

In contrast, tracking of the coronaries based on image analysis of contrasted vessels (as described in, e.g., Hoffmann K R, Sen A, Lan L, Kok-Gee C, Esthappan-J, Mazzucco M, "A system for determination of 3D vessel tree centerlines from biplane images", International Journal of Cardiac Imaging, 16(5), pp. 315-330, 2000) requires intense manual interaction and is plagued by the problem that the exact position along a vessel centerline is not available.

In consequence, a modified and dedicated flow protocol according to a first embodiment of the invention is provided. In this embodiment, a guidewire or any other interventional device with distance markers is used and navigated over a coronary segment of interest. A dedicated flow sequence is acquired. In this sequence, the patient is asked to hold his breath. Then, one cardiac cycle is imaged without contrast agent and subsequently, a small and diluted amount of contrast agent is injected. In- and outflow of this contrast agent in few cardiac cycles is imaged. The following processing is applied to such acquisitions:

The position of at least one marker upstream and one marker downstream of a suspicious vessel segment is extracted using e.g. template tracking or other well-known approaches from computer vision. The position of the markers is stored in x1(t) and x2(t), respectively.

Then, a synchronous analysis of the ECG provides the phase $\Phi_{ECG}(t)$ of the cardiac cycle for all frames in the angiogram sequence.

Furthermore, with the position of the two points known in all frames, the local x-ray attenuation TIC1(t) and TIC2(t) is extracted from the angiograms. The distance between these two points is unambiguously known even in the presence of strong bends and foreshortening because these points are located on the guidewire or interventional device.

Then, the local contrast agent concentration in the vessel is determined by comparison of the actual greylevel with the greylevel at the respective position during the first non-contrasted heart cycle.

Finally, the distance L between the two control points in the coronary is known from the geometric design of the markers. This secured distance together with the background-corrected TIC1*(t) and TIC2*(t) (which contain modified data in comparison to the TIC1(t) and TIC2(t) mentioned above) allows to apply suitable algorithms for videodensitometric blood flow assessment and, therefore, determine the amount of blood flowing through the vessel segment of interest.

In a further exemplary embodiment of the invention, a model-based method for videodensitometry is applied. In this flow model, the transport of contrast agent through a vessel segment of known length and radius is simulated. With TIC1 (t) as the observed input into this vessel segment, the model then predicts TIC2'(t) for various flow volumes, velocity profiles in the cross-section of a vessel, diffusion constants between contrast agent and blood, and a driving pressure changing over time. An optimization over these parameters tunes the model such that the prediction TIC2'(t) and the observed TIC2(t) are as similar as possible.

Then, all relevant flow information, especially the volume flow, can be read from the tuned model parameters. For coronary flow, it is necessary to work with a variable driving pressure p(t) and it could be beneficial to introduce a variable vessel radius r(t) that both change over the cardiac cycle. In consequence, the model has to additionally optimize two functions $p(\phi_{ECG})$ and $r(\phi_{ECG})$ that are synthesized from few scalar parameters, e.g. their maximal and minimal value and the moments of respective transition in the cardiac cycle. Physiologic a-priori knowledge on expected courses of $p(\phi_{ECG})$ and $r(\phi_{ECG})$ can be used as initialization such that only a match to inter-patient variabilities is required. The maximal and minimal radius of the coronary (that is partially embedded in the myocardium, therefore subject to varying external pressure) can further be estimated from angiograms acquired at respective $\phi_{ECG}$.

If the volume flow is also determined in one healthy coronary segment, it may further be possible to quantify the additional pressure decline cause by a stenosis.

As extension and further embodiments, methods are provided that allow to apply the flow analysis even to standard diagnostic angiograms.

The guidewire with distance markers may be replaced by an interventional device or a semi-opaque guidewire. The extraction of markers on interventional devices is described in Florent R, Nosjean L, Lelong P, "Medical viewing system and method for enhancing structures in noisy images", WO 03/043516 A2, 2003 and guidewire tracking with end point localization is described in Baert S, Niessen W J, Meijering E H W, Frangi A F, Viergever A F, "Guide wire tracking during endovascular interventions," in Delp S L, DiGioia A M, Jaramaz B (eds.): MICCAI 2000, Proc. LNCS 1935, pp. 727-734, 2000) for standard guidewires.

A further extension may allow to determine at least two fixed positions in a coronary in a complete contrasted angiogram acquisition even if the markers are partially obscured by a contrast agent injection that aims at the imaging of a fully opaque intravascular lumen:

Firstly, the frames of the angiogram are first classified based on the information if contrast agent is contained in the vessel of interest or not. A respective method has been described in Aach T, Condurache A, Eck K, Bredno J, "Statistical-model based identification of complete vessel-tree frames in coronary aniograms," in Bouman C A and Miller E L (eds.), Electronic Imaging 2004:Computational Imaging, Proc. SPIE 5299, pp 283-294, 2004.

Secondly, template tracking or other well-known methods (as disclosed in Baert S, Niessen W J, Meijering E H W, Frangi A F, Viergever A F, "Guide wire tracking during endovascular interventions," in Delp S L, DiGioia A M, Jaramaz B(eds.): MICCAI 2000, Proc. LNCS 1935, pp. 727-734, 2000, and in Florent R, Nosjean L, Lelong P, "Medical viewing system and method for enhancing structures in noisy images", WO 03/043516 A2, 2003) may provide the positions x1(t) and x2(t) of two points in a coronary in all frames that have been classified to contain no or few contrast agent.

Thirdly, respiration motion compensation may provide the global motion of the heart in the rib cage. For example, the depth $\phi_{Resp}(t)$ of respiration intake from projection angiograms can be used to determine a compensating shift $\Delta (\Phi_{Resp,1}, \Phi_{Resp,2})$ between frames acquired with different depth of respiration intake such that imaged coronaries are registered onto each other. This compensation is also applicable when the coronaries are currently not visible in an angiogram frame.

Using this compensation, the respiration-compensated positions x1'(t) and x2'(t) are computed from x1(t), x2(t), and $\Phi_{Resp}(t)$ to depend only on the heart beat and no longer on respiration.

Above information is then combined to create the curves x1 $(\Phi_{ECG}, \Phi_{Resp})$ and x2$(\Phi_{ECG}, \Phi_{Resp})$ that determine the position of two fixed points in a coronary at arbitrary phases in the cardiac cycle and for varying depth of respiration intake.

The positions x1(t) and x2(t) can now be computed for all frames in which the markers are not visible due to contrast agent in the vessel. A local adaptive matching to the centerline of the coronary can correct for small deviations that result from this prediction.

When x1(t) and x2(t) have been extracted over the full angiogram duration, the videodensitometric analysis described for the first embodiment can be applied with no further modification.

According to an aspect of the invention, coronary motion compensation is provided from the position of the visible markers for a dedicated flow acquisition in which only diluted contrast agent is used. For standard angiograms with fully opaque vessels, further already presented motion compensation methods for heartbeat and respiration are applied. Following the coronary motion compensation, it is possible to collect time-intensity curves (TICs) of contrast agent concentration from at least two well-defined points in a moving coronary. This information is sufficient for a model-based flow analysis that is specially adapted to determine the total volume flow, the pressure decline, and further relevant parameters in a vessel even in the presence of strong pulsation effects.

Figure 3:
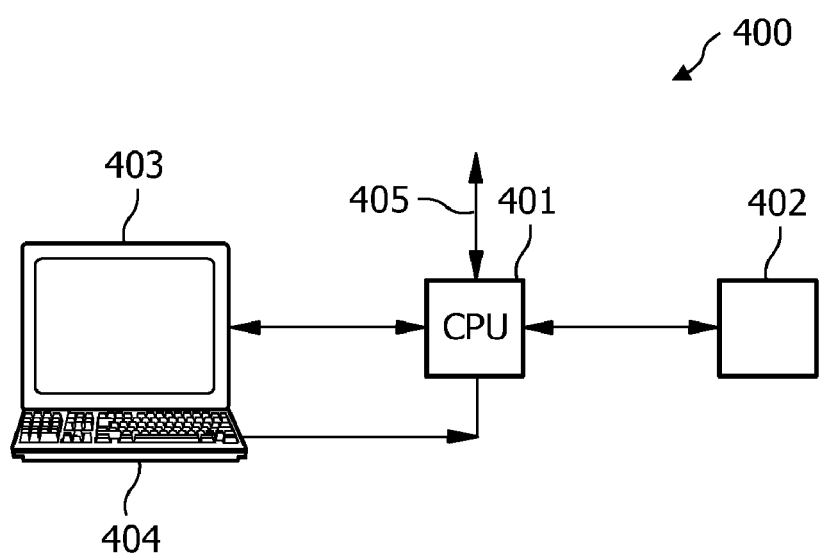
FIG. 3 shows an exemplary embodiment of an image processing device according to the present invention, for executing an exemplary embodiment of a method in accordance with the present invention.

FIG. 3 depicts an exemplary embodiment of a data processing device 400 according to the present invention for executing an exemplary embodiment of a method in accordance with the present invention. The data processing device 400 depicted in FIG. 3 comprises a central processing unit (CPU) or image processor 401 connected to a memory 402 for storing an image depicting an object of interest, such as a coronary artery or other moving objects that hold a fluid.

The data processor 401 may be connected to a plurality of input/output network or diagnosis devices, such as a x-ray imager. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram unit.

The proposed model for coronary blood flow analysis may be implemented on a workstation available in a coronary Cathlab, such as a workstation dedicated to provide additional functionalities for imaging, diagnosis, treatment decision and outcome control.

All processing functions may, according to the invention, be integrated into a common Cathlab workstation. The interventionalist may use a method to select a coronary for further diagnosis and treatment, which is to navigate a guidewire and possible interventional devices into this vessel. Following a diagnostic contrasted angiogram or a dedicated flow acquisition, the algorithm for blood flow assessment may start automatically and provide the flow volume in this vessel of interest.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. Examination apparatus (100) for motion compensated determination of a flow dynamics from an image sequence of an object of interest (15, 107), the examination apparatus (100) comprising:
   an analysis unit (118) adapted for performing a determination of a first flow dynamics in a region of the object of interest (15, 107);
   wherein the determination comprises a motion compensation performed on the basis of a tracking of a first position of a first marker and a second position of a second marker in the image sequence;
   wherein the first and second markers are distance markers of an interventional device; and
   wherein a motion of the markers corresponds to a motion of the object of interest.

2. The examination apparatus (100) of claim 1,
   further comprising an acquisition unit (108) adapted for acquiring the image sequence in one of a dedicated flow run and a standard acquisition run.

3. The examination apparatus (100) of claim 2,
   wherein the image sequence is acquired according to the following scheme:
   acquisition of first data during a cardiac cycle;
   application of a small and diluted amount of contrast agent; and
   subsequent acquisition of second data corresponding to an inflow and outflow of the contrast agent during a multitude of cardiac cycles.

4. The examination apparatus (100) of claim 1,
   wherein the image sequence is an angiogram data set.

5. The examination apparatus (100) of claim 1,
   wherein the motion compensation comprises the use of heartbeat data, respiration data, voluntary and involuntary patient motion data.

6. The examination apparatus (100) of claim 1,
   wherein the analysis unit (118) is further adapted for:
   determining a time intensity curve of a contrast agent concentration on the basis of at least the first position of the first marker and the second position of the second marker; and
   performing a model-based flow analysis adapted to determine at least one of a total volume flow and a pressure decline, even in the presence of strong pulsation effects.

7. The examination apparatus (100) of claim 6,
   wherein the model-based flow analysis includes varying flow speeds over the cardiac cycle and compensates for such pulsatility when electrocardiogram data is available as input.

8. The examination apparatus (100) of claim 1,
   wherein the object of interest (15, 107) is a coronary artery; and
   wherein the region of the object of interest (15, 107) is a first vessel segment of the coronary artery.

9. The examination apparatus (100) of claim 1,
   wherein the interventional device is one of a guide wire, a semi-transparent guide wire, a stenting device, and a ballooning device.

10. The examination apparatus (100) of claim 1,
   wherein the analysis unit (118) is further adapted for:
   compensating a variability of the first volume flow over the cardiac cycle by one of a defined time of contrast agent injection or by an inclusion and compensation of the variability in a subsequent analysis.

11. The examination apparatus (100) of claim 10,
   wherein the subsequent analysis is a videodensitometric analysis.

12. The examination apparatus (100) of claim 1,
   wherein the analysis unit (118) is further adapted for:
   determining a second volume flow in a second vessel segment of the coronary artery; and
   determining a pressure decline in the first vessel segment on the basis of the second volume flow.

13. The examination apparatus (100) of claim 1,
   wherein the examination apparatus (100) is adapted as one of a Cathlab imager in fixed imaging geometry, a 3D computed tomography apparatus, and a 3D rotational X-ray apparatus.

14. The examination apparatus (100) of claim 1, configured as one of the group consisting of a material testing apparatus and a medical application apparatus.

15. A method of motion compensated determination of a flow dynamics from an image sequence of an object of interest (15, 107) with an examination apparatus, method comprising the step of:
   determining of a first flow dynamics in a region of the object of interest (15, 107);

wherein the determination comprises a motion compensation performed on the basis of a tracking of a first position of a first marker and a second position of a second marker in the image sequence; and wherein a motion of the markers corresponds to a motion of the object of interest;

determining a time intensity curve of a contrast agent concentration on the basis of at least the first position of the first marker and the second position of the second marker; and performing a model-based flow analysis adapted to determine at least one of a total volume flow and a pressure decline;

wherein the model-based flow analysis includes varying flow speeds over the cardiac cycle and compensates for such pulsatility when electrocardiogram data is available as input.

16. A computer-readable medium (402), in which a computer program of motion compensated determination of a flow dynamics from an image sequence of an object of interest (15, 107) is stored which, when being executed by a processor (401), is adapted to carry out the step of:

determining of a first flow dynamics in a region of the object of interest (15, 107);

wherein the determination comprises a motion compensation performed on the basis of a tracking of a first position of a first marker and a second position of a second marker in the image sequence; and wherein a motion of the markers corresponds to a motion of the object of interest; and compensating a variability of the first volume flow over a cardiac cycle by a defined time of contrast agent injection.

17. A program element of motion compensated determination of a flow dynamics from an image sequence of an object of interest (15, 107), which, when being executed by a processor (401), is adapted to carry out the step of:

determining of a first flow dynamics in a region of the object of interest (15, 107);

wherein the determination comprises a motion compensation performed on the basis of a tracking of a first position of a first marker and a second position of a second marker in the image sequence; and wherein a motion of the markers corresponds to a motion of the object of interest; and compensating a variability of the first volume flow over a cardiac cycle by an inclusion and compensation of the variability in a videodensitometric analysis.

* * * * *